(12) United States Patent
Huang et al.

(10) Patent No.: US 6,750,603 B2
(45) Date of Patent: Jun. 15, 2004

(54) SECOND ORDER NONLINEAR OPTICAL CHROMOPHORES AND ELECTRO-OPTIC DEVICES THEREFROM

(75) Inventors: Diyun Huang, Bothell, WA (US); Baoquan Chen, Bothell, WA (US)

(73) Assignee: Lumera Corporation, Bothell, WA (US)

( * ) Notice: Subject to any disclaimer, the term of this patent is extended or adjusted under 35 U.S.C. 154(b) by 0 days.

(21) Appl. No.: 10/301,978

(22) Filed: Nov. 22, 2002

(65) Prior Publication Data

US 2003/0107027 A1 Jun. 12, 2003

Related U.S. Application Data

(63) Continuation-in-part of application No. 09/932,831, filed on Aug. 17, 2001
(60) Provisional application No. 60/226,267, filed on Aug. 17, 2000.

(51) Int. Cl.$^7$ .............................. H01J 1/62; G02B 26/00

(52) U.S. Cl. ..................... 313/483; 359/326; 359/237; 385/2; 385/122; 385/141; 430/630

(58) Field of Search ......................... 313/483; 359/326, 359/237; 385/2, 122, 141; 430/630

(56) References Cited

U.S. PATENT DOCUMENTS

| | | | |
|---|---|---|---|
| 4,028,702 A | 6/1977 | Levine | |
| 4,258,386 A | 3/1981 | Cheung | |
| 5,041,516 A | 8/1991 | Fréchet et al. | |
| 5,051,754 A | 9/1991 | Newberg | |
| 5,198,513 A | 3/1993 | Clement et al. | |
| 5,207,952 A | 5/1993 | Griffin, III | |
| 5,223,356 A | 6/1993 | Kumar et al. | |
| 5,266,365 A | 11/1993 | Kester et al. | |
| 5,353,033 A | 10/1994 | Newberg et al. | |
| 5,359,008 A | 10/1994 | Amano et al. | |
| 5,433,895 A | 7/1995 | Jeng et al. | |
| 5,520,968 A | 5/1996 | Wynne et al. | |
| 5,635,576 A | 6/1997 | Foll et al. | |
| 5,670,091 A | 9/1997 | Marder et al. | |
| 5,679,763 A | 10/1997 | Jen et al. | |
| 5,696,243 A | 12/1997 | Beckmann et al. | |
| 5,714,304 A | 2/1998 | Gibbons et al. | |
| 5,776,374 A | 7/1998 | Newsham et al. | |
| 5,783,649 A | 7/1998 | Beckmann et al. | |
| 5,811,507 A | 9/1998 | Chan et al. | |
| 5,861,976 A | 1/1999 | Hoekstra | |
| 6,067,186 A | 5/2000 | Dalton et al. | |
| 6,090,332 A | 7/2000 | Marder et al. | |
| 6,126,867 A | 10/2000 | Kanitz et al. | |
| 6,130,339 A | 10/2000 | Tan et al. | |
| 6,197,921 B1 * | 3/2001 | Tan et al. ................... 528/380 |
| 6,228,977 B1 | 5/2001 | Kanitz et al. | |
| 6,294,573 B1 | 9/2001 | Curtin et al. | |
| 6,403,809 B1 * | 6/2002 | Holmes et al. ............... 549/41 |

FOREIGN PATENT DOCUMENTS

| | | |
|---|---|---|
| DE | 44 01 911 A1 | 8/1995 |
| DE | 44 16 476 A1 | 11/1995 |
| DE | 195 32 828 A1 | 3/1996 |
| EP | 0 414 185 A2 | 2/1991 |
| EP | 0 637 774 A1 | 2/1995 |
| EP | 0 729 056 A1 | 8/1996 |
| EP | 0 754 709 A1 | 1/1997 |
| JP | 8-108624 | 4/1996 |
| JP | 2000-89268 | 3/2000 |
| JP | 2001-85713 | 3/2001 |

OTHER PUBLICATIONS

Kim et al., "Nonlinear optical chromophores containing dithienothiophene as a new type of electron relay," *J. Mater. Chem*, 1999 9: 2227–2232.

Kojima et al., "Facile Synthesis of Thiophene Derivatives Using a Cyclopropenyl Cation," *Synthesis*, 1996, 1193–1195.

Raimundo et al., "Push–pull chromophores based on 2,2'–bi(3,4–ethylenedioxythiophene) (BEDOT) π–conjugating spacer," *Tetrahedron Letters*, 2001, 42:1507–1510.

Reinhardt et al., "Highly Active Two–Photon Dyes: Design, Synthesis, and Characterization toward Application," *Chem. Mater.*, 1998, 10:1863–1874.

Bosman et al., "About Dendrimers: Structure, Physical Properties, and Applications," *Chem. Rev.*, 1999, 99:1665–1688.

Chen et al., "Thermosetting Polyurethanes with Stable and Large Second–Order Optical Nonlinearity," *Macromolecules*, 1992, 25: 4032–4035.

Gorman and Marder, "An investigation of the interrelationships between linear and nonlinear polarizabilities and bond–length alternation in conjugated organic molecules," *Proc. Natl. Acad. Sci. USA*, 1993, 90:11297–11301.

Landmesser et al., "Regiocontrolled C–8 Acylation of Castanospermine," *Synthetic Comm.*, 1996, 26(11):2213–2221.

Ma et al., "A Convenient Modular Approach of Functionalizing Aromatic Polyquinolines for Electrooptic Devices," *Chem. Mater.*, 1999, 11:2218–2225.

(List continued on next page.)

*Primary Examiner*—Deborah C Lambkin
(74) *Attorney, Agent, or Firm*—Fish & Richardson P.C., P.A.

(57) ABSTRACT

A nonlinear optical chromophore having the formula D-π-A, wherein π is a π bridge including a thiophene ring having oxygen atoms bonded directly to the 3 and 4 positions of the thiophene ring, D is a donor, and A is an acceptor.

21 Claims, 7 Drawing Sheets

OTHER PUBLICATIONS

Ma et al., "A Novel Class of High–Performance Perfluorocyclobutane–Containing Polymers for Second–Order Nonlinear Optics," *Chem. Mater.,* 2000, 12:1187–1189.

Ma et al., "Highly Efficient and Thermally Stable Nonlinear Optical Dendrimer for Electrooptics," *J. Am. Chem. Soc.,* 2001, 123:986–987.

Mao et al, "Progress toward Device–Quality Second–Order Nonlinear Optical Materials. 1. Influence of Composition and Processing Conditions on Nonlinearity, Temporal Stability, and Optical Loss," *Chem. Mater.,* 1998, 10:146–155.

March, "Appendix B: Classification of Reactions by Type of Compound Synthesized," *Advanced Organic Chemistry,* 1992, John Wiley & Sons, Inc., New York, pp. 1269–1300.

Smith and Babb, "Perfluorocyclobutane Aromatic Polyethers. Synthesis and Characterization of New SiloxaneContaining Fluoropolymers," *Macromolecules,* 1996, 29:852–860.

* cited by examiner

US 6,750,603 B2

SECOND ORDER NONLINEAR OPTICAL CHROMOPHORES AND ELECTRO-OPTIC DEVICES THEREFROM

RELATED APPLICATIONS

This application is a continuation-in-part of patent application Ser. No. 09/932,831 filed Aug. 17, 2001, entitled "Design and Synthesis of Advanced NLO Materials for Electro-Optic Applications," which is assigned to the same assignee as the present application, which claims benefit of Provisional Application No. 60/226,267 filed Aug. 17, 2000, and which is hereby incorporated by reference in its entirety.

All patents, patent applications, and publications cited within this application are incorporated herein by reference to the same extent as if each individual patent, patent application or publication was specifically and individually incorporated by reference.

BACKGROUND OF THE INVENTION

The invention relates generally to the organic chromophores for second order nonlinear optical (NLO) applications, compositions including such chromophores, and applications including such chromophores and compositions.

The development and uses of NLO chromophores, including polymer matrix development, waveguide fabrication, and optical device fabrication are well documented. An NLO chromophore (also known as a "push-pull" chromophore) comprises three fundamental building blocks represented by the general formula D-π-A, where D is a donor, π is a π-bridge, and A is an acceptor. In the art, a "π-bridge" is sometimes referred to as a "π-conjugated bridge," "π-electron bridge," "conjugated π-electron bridge," and the like. Examples of such bridges are described, for example, in U.S. Pat. Nos. 5,670,091, 5,679,763, 6,067,186, and 6,090,332. A "π-bridge" allows charge transfer from a donor to an acceptor in a chromophore. Exemplary acceptors are shown in FIG. 1, where, independently at each occurrence, $R^1$ is hydrogen, a halogen except when bonded to a carbon alpha to or directly to a nitrogen, oxygen, or sulfur atom, or an alkyl, aryl, heteroalkyl, or heteroaryl group; Y is O, S or Se; and q is 0 or 1. Exemplary donors are shown in FIG. 2, where, independently at each occurrence, $R^1$ is hydrogen, a halogen except when bonded to a carbon alpha to or directly to a nitrogen, oxygen, or sulfur atom, or an alkyl, aryl, heteroalkyl, or heteroaryl group; $R^2$ is hydrogen or an alkyl, aryl, heteroalkyl, or heteroaryl group; Y is O, S or Se; m is 2, 3 or 4; p is 0, 1 or 2; and q is 0 or 1. Herein, a heteroalkyl group includes, but is not limited to, functional groups, halogen substituted alkyl groups, perhalogenated alkyl groups, and dendrons. What is meant by a functional group in generally understood in the art of organic chemistry, for example see Appendix B in Jerry March, "Advanced Organic Chemistry" $4^{th}$ Edition, John Wiley and Sons, New York, pp 1269–1300. A "dendron" is a substituent that has regularly repeating subunits. A dendron may be further comprised of one or more heteroaryl group. A "dendrimer" is a macromolecular structure that contains a "core" surrounded by one or more dendrons. Often in the art, the terms dendron and dendrimer are used interchangeably. Dendrons and dendrimers are illustrated and discussed in Bosman et al., *Chem. Rev.* 1999, 99, 1665 and U.S. Pat. No. 5,041,516.

The particular D-π-A arrangement affects the ability of the molecule to achieve large second order NLO effects. Thus, the first molecular electronic hyperpolarizability (β, sometimes given as μβ, where μ is the dipole moment of the chromophore), which is a measure of this ability, can be tuned and optimized by changing the electronic properties of any one of D, π, or A, see Gorman and Marder *Proc. Natl. Acad. Sci, USA* 1993, 90, 11297. Molecular NLO effects, in turn, can be translated into bulk EO activity in a material by aligning molecules in one direction by applying an electric field.

SUMMARY OF THE INVENTION

In one aspect, a nonlinear optical chromophore has the formula D-π-A where π is a π bridge including a thiophene ring having oxygen atoms bonded directly to the 3 and 4 positions of the thiophene ring, D is a donor, and A is an acceptor. The oxygens bonded directly to the 3 and 4 ring positions of the of the thiophene ring may be further independently substituted with an alkyl group comprising 1 to about 20 carbons, a heteroalkyl group comprising 1 to about 20 carbons, an aryl group comprising 1 to about 20 carbons, or a heteroaryl group comprising 1 to about 20 carbons.

In a second aspect, a nonlinear optical chromophore has the formula:

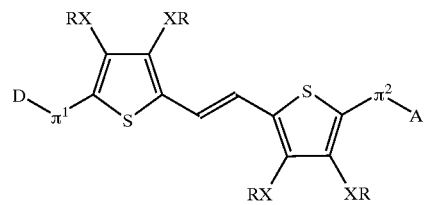

wherein, independently at each occurrence: $\pi^1$ is absent or a π-bridge; $\pi^2$ is absent or a π-bridge; D is an donor; A is an acceptor; X is O or S; and R is an alkyl group comprising 1 to about 20 carbons, a heteroalkyl group comprising 1 to about 20 carbons, an aryl group comprising 1 to about 20 carbons, or a heteroaryl group comprising 1 to about 20 carbons. These chromophores may be combined with a polymer matrix to form second order nonlinear optical compositions useful in a variety of applications, including electro-optic devices such as optical modulators, optical switches, and optical directional couplers. For example, the chromophore and polymer matrix may contain crosslinkable functional groups, and may be combined to form a guest-host composite, in which the chromophore is the guest and the polymer matrix is the host. An electric field is then applied to the composite to induce electro-optic activity, after or during which the composite is crosslinked to covalently bond the chromophore to the polymer matrix. Other features and advantages of the invention will be apparent from the following description of preferred embodiments thereof, and from the claims.

Figure 1:
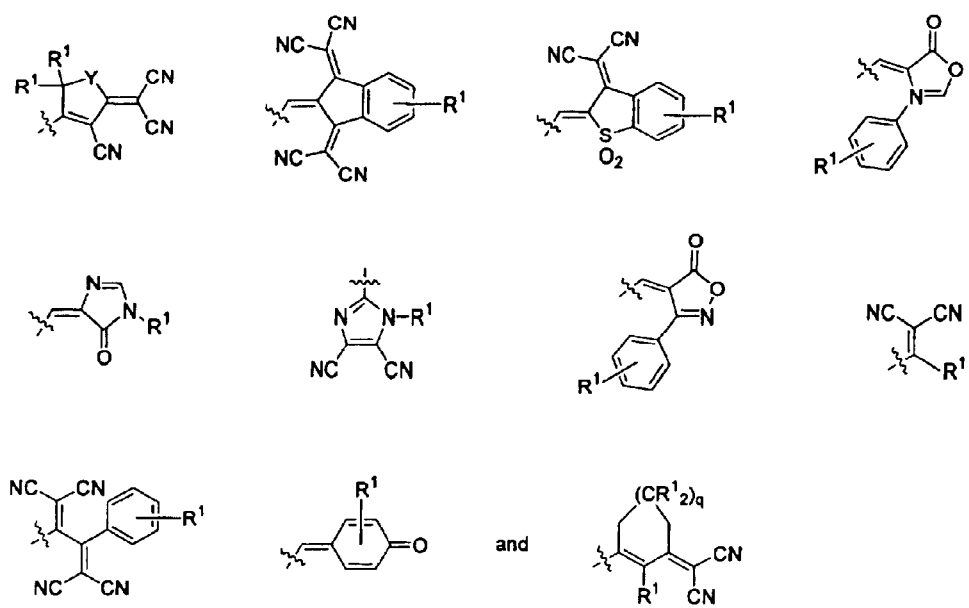
FIG. 1 illustrates exemplary acceptors that can be used in some embodiments.
Figure 2:
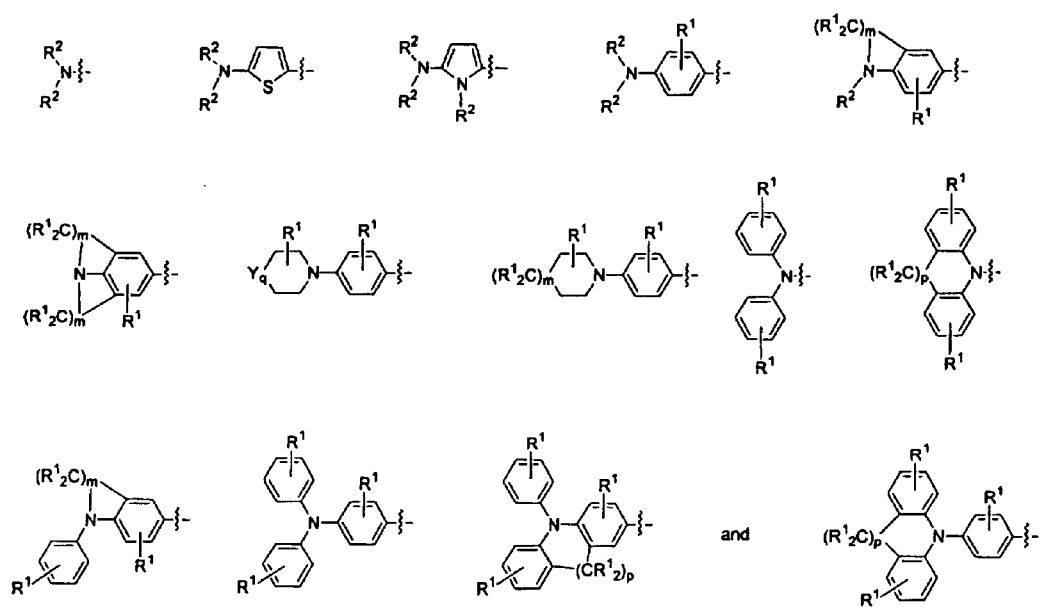
FIG. 2 illustrates exemplary donors that can be used in some embodiments.

DETAILED DESCRIPTION
The second order nonlinear optical chromophores have the chemical structures and formulas described above in the Summary of the Invention. Examples of donors (D) that may be used include structures chosen from the group consisting of
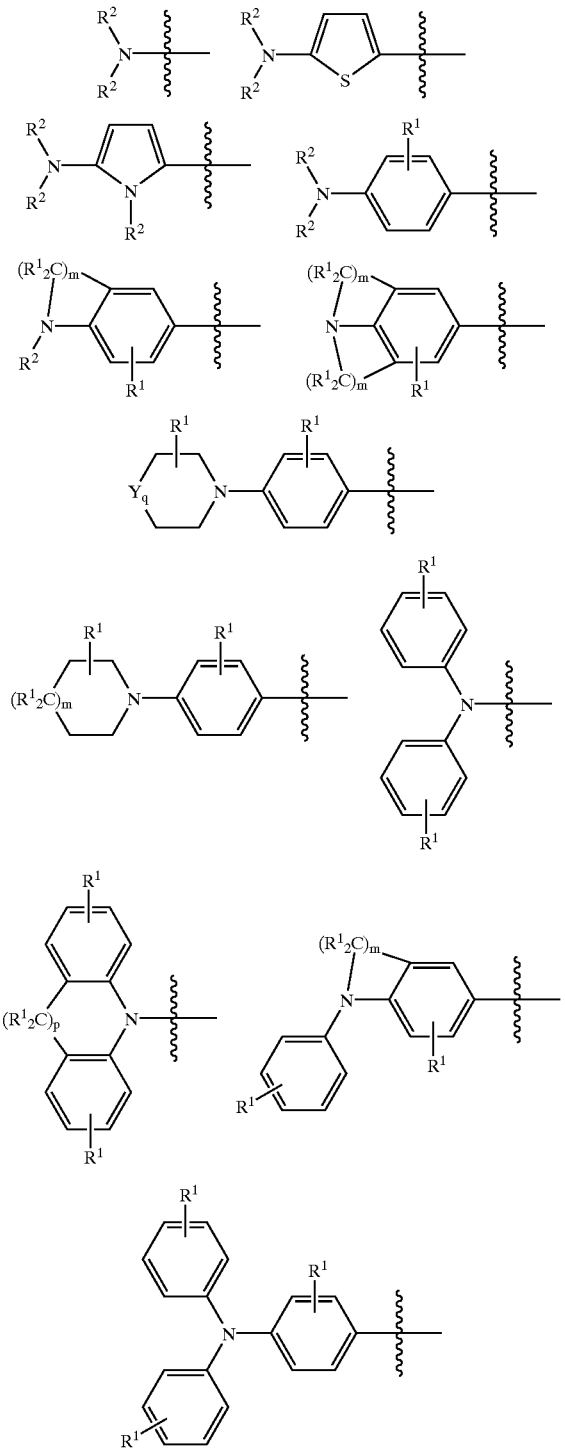
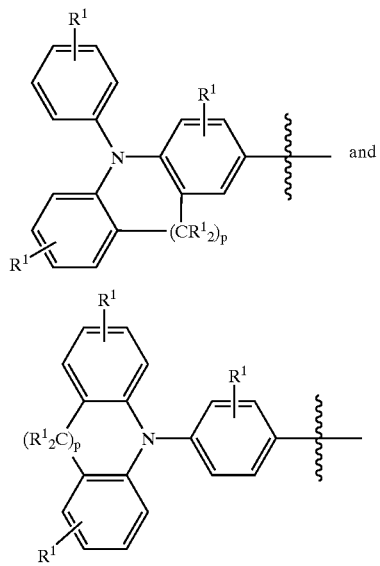
Examples of acceptors (A) that may be used include structures selected from the group consisting of
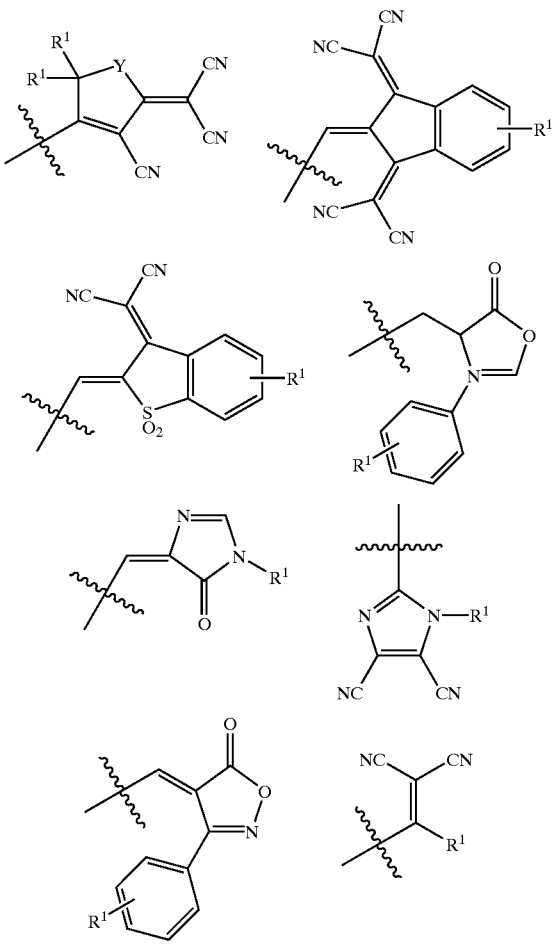

-continued

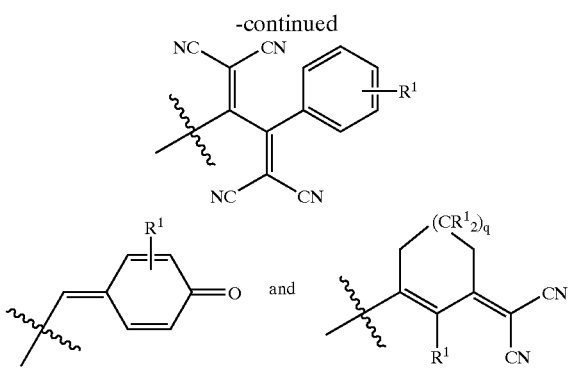

wherein independently at each occurrence: $R^1$ is hydrogen, a halogen except when bonded to a carbon alpha to or directly to a nitrogen, oxygen, or sulfur atom, or an alkyl, aryl, heteroalkyl, or heteroaryl group; $R^2$ is hydrogen or an alkyl, aryl, heteroalkyl, or heteroaryl group; Y is O, S or Se; m is 2, 3 or 4; p is 0, 1 or 2; and q is 0 or 1. Preferably, the donor is chosen from the group consisting of

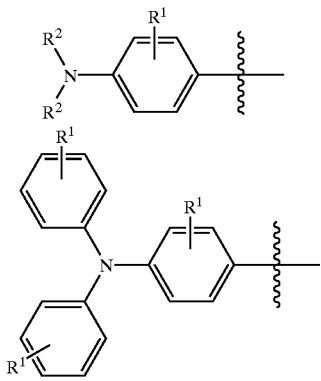

wherein independently at each occurrence: $R^1$ is hydrogen, a halogen except when bonded to a carbon alpha to or directly to a nitrogen, oxygen, or sulfur atom, or an alkyl, aryl, heteroalkyl, or heteroaryl group; and $R^2$ is hydrogen or an alkyl, aryl, heteroalkyl, or heteroaryl group.

The chromophores may be combined with a polymer matrix to form compositions useful in a variety of electro-optical applications. Such compositions may be prepared according to a number of known techniques, including those described in U.S. Pat. Nos. 5,776,374; 5,714,304; 5,223,356; 5,433,895; 6,294,573; 6,126,867; 5,811,507; 5,635,576; 5,520,968; 5,359,008; 5,266,365; 5,207,952; and 6,228,977 and *Chem. Mater.* 2000, 12, 1187; *J. Am Chem. Soc.* 2001, 123, 986; *Macromolecules* 1992, 25, 4032; *Chem. Mater.* 1999, 11, 2218; and *Chem. Mater.* 1998, 10, 146. In one embodiment, the chromophore is a guest in the crosslinked polymer matrix host. In another embodiment, the chromophore is covalently incorporated into a crosslinked polymer matrix, the chromophore being at first a guest in a crosslinkable polymer matrix host.

Another embodiment is a process comprising: 1) providing a guest chromophore in a polymer host, wherein both the guest chromophore and polymer host contain fluorinated crosslinkable groups; 2) applying an electric field to the composite to induce electro-optic activity; and 3) crosslinking the composite, whereby the chromophore guest is covalently incorporated into the polymer host to provide a crosslinked nonlinear optical material. This method has advantages over other conventional processes, such as: 1) the chromophore guest and polymer host are compatible due to both having fluorinated crosslinkable groups; 2) the nonlinear optical material produced will have lower loss at 1550 nm since the crosslinking groups are fluorinated; 3) the chromophore host has more degrees of freedom to align with the poling field since it is not covalently incorporated into the polymer host before the poling filed is applied; and 4) the molecular weight and composition of the polymer are precisely known, which will allow control of critical parameters like film thickness, $T_g$, and solubility.

The nonlinear optical compositions may be used to fabricate optical devices, optical switches, modulators, waveguides, or other electro-optical devices that can be used in communication systems using methods known in the art. For example, in optical communication systems, devices fabricated including compositions described above may be incorporated into routers for optical communication systems, waveguides for optical communication systems, or for optical switching or computing applications. Because polymers are generally less demanding than currently used materials, devices including compositions described above may be more highly integrated.

Specific examples of components of optical communication systems that may be fabricated in whole or in part from the nonlinear optical compositions described above include, without limitation, straight waveguides, bends, single-mode splitters, couplers (including directional couplers, MMI couplers, star couplers), routers, filters (including wavelength filters), switches, modulators (optical and electro-optical, e.g., birefringent modulator, the Mach-Zender interferometer, and directional and evanescent coupler), arrays (including long, high-density waveguide arrays), optical interconnects, optochips, single-mode DWDM components, and gratings.

Waveguides made with nonlinear optical compositions described above may be used in telecommunication, data communication, signal processing, information processing, and radar system devices and thus may be used in communication methods relying, at least in part, on the optical transmission of information. Specific applications in which the above-described nonlinear optical compositions can be incorporated include:

(1) an electro-optic device that is an interferometric optical modulator or switch, comprising: 1) an input waveguide; 2) an output waveguide; 3) a first leg having a first end and a second end, the first leg being coupled to the input waveguide at the first end and to the output waveguide at the second end; and 4) and a second leg having a first end and a second end, the second leg being coupled to the input waveguide at the first end and to the output waveguide at the second end, wherein at least one waveguide includes a nonlinear optical composition described above.

(2) an optical modulator or switch, comprising: 1) an input; 2) an output; 3) a first waveguide extending between the input and output; and 4) a second waveguide aligned to the first waveguide and positioned for evanescent coupling to the first waveguide; wherein at least one waveguide includes a nonlinear optical composition described above.

(3) an optical router that includes at least one optical modulator, optical switch, or optical directional coupler comprising a nonlinear optical composition described above.

Additional applications include a communications system including at least one electro-optic device comprising a nonlinear optical composition described above, a method of data transmission including transmitting light through a nonlinear optical composition described above, a method of telecommunication including transmitting light through a nonlinear optical composition described above, a method of transmitting light including directing light through or via a nonlinear optical composition described above, and a method of routing light through an optical system comprising transmitting light through or via a nonlinear optical composition described above.

Additionally, the nonlinear optical compositions described herein may be applied to devices or methods that control the phase of light waves passing through the material. In some applications, electrical fields are applied across a set of waveguides through which the light waves travel. Controlling the electrical fields allows the relative phases of the light waves to be controlled. Such approaches are particularly useful in applications known in the art such as phased-array radar or phase matching of light waves passing through alternative waveguides, for example see, U.S. Pat. Nos. 5,353,033; 5,051,754; 4,258,386; and 4,028,702. Thus, another embodiment is a phased-array radar comprising a nonlinear optical composition embodiment described above.

The following examples are illustrative and are not intended as a limitation thereof.

EXAMPLES

Example 1

Figure 3:
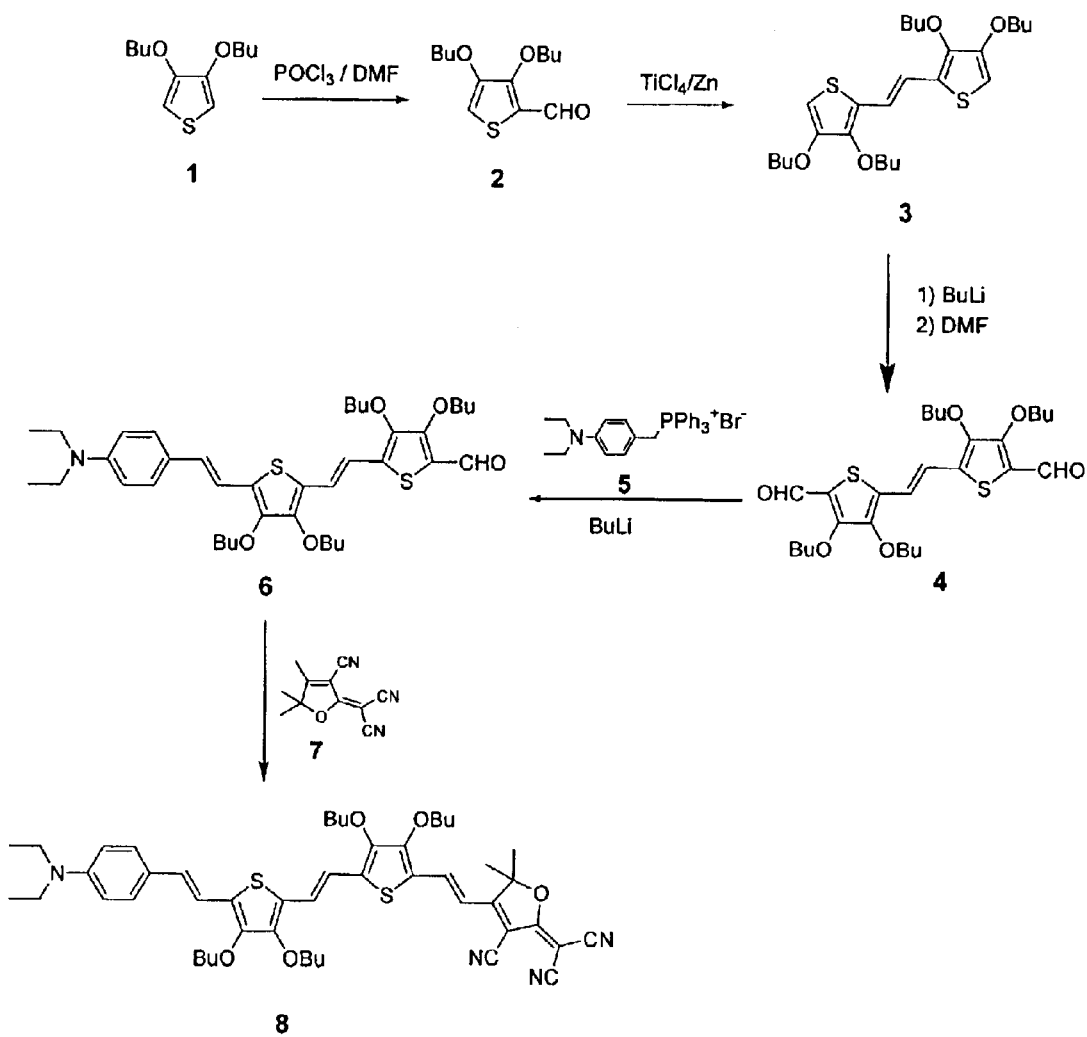
FIGS. 3–6 outline syntheses of various nonlinear optical chromophores.

Referring to FIG. 3, Compound 1, which was prepared as in Syn. Comm. 1996, 26, 2213, (187.8 g, 0.824 mol), dry DMF (127.4 mL, 1.647 mol) and dry dichloromethane (2000 mL) were mixed in a 3-neck flask and cooled to 0° C. POCl$_3$ (201.6 g, 1.318 mol) was added. The mixture was heated to reflux for 3 h. Then it was poured into 1 M NaOAc solution. It was extracted with CH$_2$Cl$_2$, washed with water and dried over MgSO$_4$. After removing the solvent, it was purified by flash column with ethyl acetate/hexane (1:2.5) to give 200 g (95%) of Compound 2.

Zinc (61.5 g, 0.941 mol) and dry THF (950 mL) were placed in a 3-neck flask and cooled to 0° C. TiCl$_4$ (51.5 mL, 0.469 mol) was added slowly. The mixture was then heated to reflux for half hour. It was then cooled to 0° C. A solution of compound 2 (60 g, 0.234 mol) and pyridine (49.5 mL, 0.605 mol) in THF (200 mL) was added slowly. The mixture was heated to reflux for 2 h. After cooling to room temperature, ice and CH$_2$Cl$_2$ were added. The resulting mixture was filtered through zelite, washed with HCl solution, water and dried over MgSO$_4$. After removing the solvent, the crude solid was purified by recrystallization from methanol to give 42.4 g (75%) of Compound 3.

Compound 3 (75 g, 0.156 mol) and ether (1400 mL) were placed in a flask and cooled to 0° C. BuLi (2.5 M) (156 mL, 0.39 mol) was added slowly and stirred for 15 min. DMF (57 mL, 0.733 mol) was then added, after which the mixture was warmed to room temperautre and stirred. NH$_4$Cl solution was added and the solvent was partially removed under reduced pressure. It was then extracted with CH$_2$Cl$_2$, washed with water, and dried over MgSO$_4$. After removing the solvent, the crude product was purified by recrystallization from methanol to give 76 g (91%) of Compound 4.

Compound 5 (2.74 g, 5.44 mmol) and THF (200 mL) were mixed and stirred. At −40° C., BuLi (2.5 M) (2.4 mL, 5.98 mmol) was added and then stirred at room temperature for 30 min. The resulting solution was added slowly to a solution of Compound 4 (2.65 g, 4.94 mmol) in 100 mL THF with stirring. The solution was stirred at room temperature for 8 h, after which the solvent was removed at reduced pressure. The remaining crude material was purified by column chromatography with hexane/CH$_2$Cl$_2$/ethyl acetate mixture to give 2.65 g (76%) of Compound 6 (which may have a slight impurity of di-reacted product).

Compound 6 (2.65 g, 3.9 mmol), Compound 7 (1.55 g, 7.8 mmol), CHCl$_3$ (2 mL), and piperidine (2 drops) were mixed and refluxed for 3 h. The reaction was monitored with thin layer chromatography until the bulk color changed to dark blue/green. The product was purified by flash column and regular column chromatography with CH$_2$Cl$_2$/ethyl acetate/hexane mixture to give 1.5 g (45%) of Compound 8.

An electro-optic polymer thin film including chromophore Compound 8 was prepared by: 1) obtaining a solution of Compound 8 and poly [biphenyl A carbonate-co-4,4'-(3,3,5-trimethylcyclohexylidene)-diphenol carbonate] from Aldrich (27% by weight loading of Compound 8 with respect to the polycarbonate) in dibromomethane (6.67% by weight loading of the dibromomethane with respect to Compound 8 and the polycarbonate); 2) spin depositing the solution at 500 rpm for 5 sec and 1500 rpm for 30 sec on a 2" diameter indium tin oxide (ITO) substrate; 3) sputtering a gold electrode on the polymer thin film; and 4) poling at 124° C. for 5–10 min in silicon oil with a poling voltage of 100–150 V/μm.

Example 2

Figure 4:
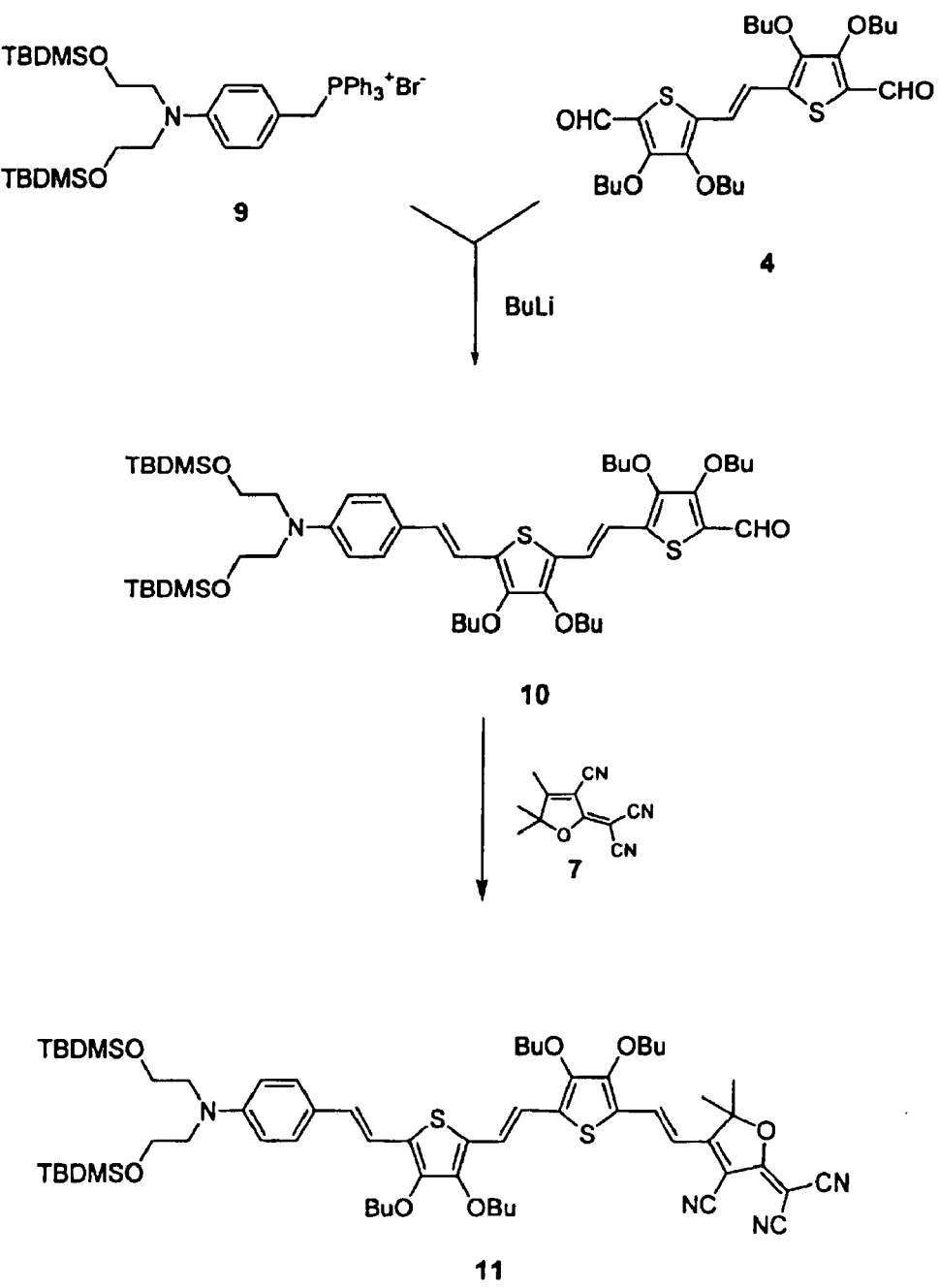
Figure 5:
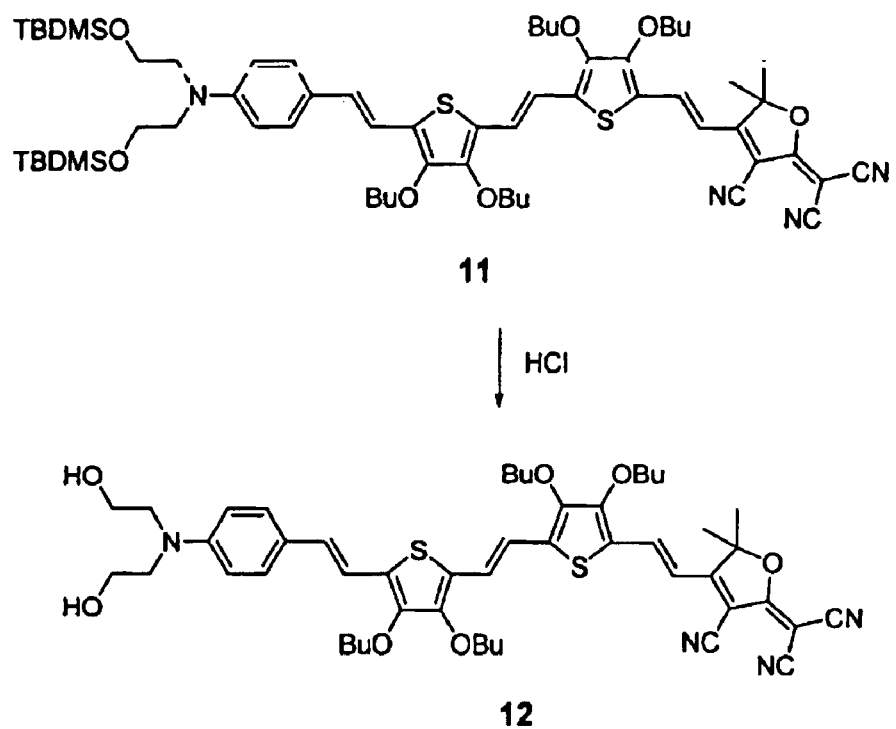
Figure 6:
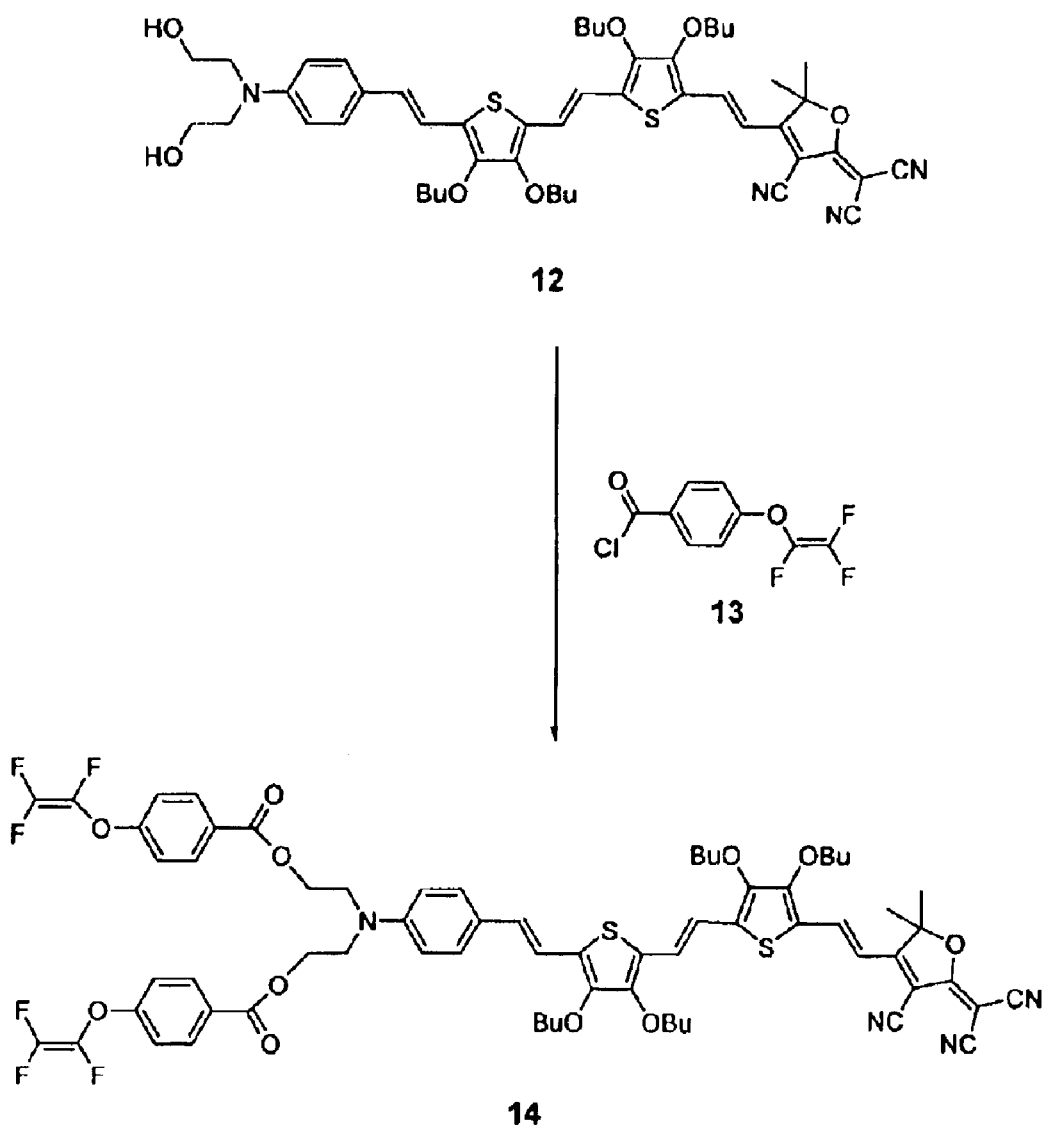

Referring to FIGS. 4–6, Compound 9 (82 g, 0.107 mol) and THF (2500 mL) were mixed and stirred. At −40° C., BuLi (2.5 M) (47.4 mL, 0.118 mol) was added and then stirred at room temperature for 30 min. The resulting solution was added slowly to a solution of Compound 4 (50 g, 0.093 mol) dissolved in 1500 mL THF. The resulting solution was then stirred at room temperature for 8 h. The solvent was removed at reduced pressure. The remaining crude material was purified by column chromatography with hexane/CH$_2$Cl$_2$/ethyl acetate mixture to give 61.3 g (70%) of Compound 10.

Compound 10 (61 g, 0.065 mol), Compound 7 (26 g, 0.129 mol), CHCl$_3$ (20 mL) and piperidine (10 drops) were mixed and refluxed for 3 h. The reaction was monitored with thin layer chromatography until the bulk color changed to dark blue/green. The product was purified by flash column and regular column chromatography with CH$_2$Cl$_2$/ethyl acetate/hexane mixture to give 36 g (49%) of Compound 11.

Compound 11 was dissolved in 750 mL THF. HCl solution (1 N, 250 mL) was added and the resulting solution was stirred for 8 h. After checking the reaction with thin layer chromatography, NaHCO$_3$ solution was added. The resulting solution was then extracted with CH$_2$Cl$_2$, washed with water, and dried over MgSO$_4$. After removing the solvent under reduced pressure, the remaining material was purified by flash column chromatography with CH$_2$Cl$_2$/ethyl acetate mixture to give 17.8 g (63%) of Compound 12.

Compound 13, which can be prepared as in U.S. Pat. No. 5,198,513 or by carbonylation of the lithium salt of Compound 15 (FIG. 7) followed by reaction with thionyl chloride, (23.5 g, 0.099 mol) was dissolved in 50 mL CH$_2$Cl$_2$ and cooled to 0° C. Compound 12 (17.8 g, 0.0199 mol) and pyridine (9.6 mL, 0.119 mol) were dissolved in 200 mL CH$_2$Cl$_2$ and added slowly to the solution of Compound 13. The resulting solution was stirred at room temperature for 8 h. The mixture was then extracted with CH$_2$Cl$_2$, washed with water, and dried over MgSO$_4$. After removing the solvent under reduced pressure, the remaining material was purified by flash column chromatography with CH$_2$Cl$_2$/ethyl acetate mixture to give 21 g (83%) of Compound 14.

Figure 7:
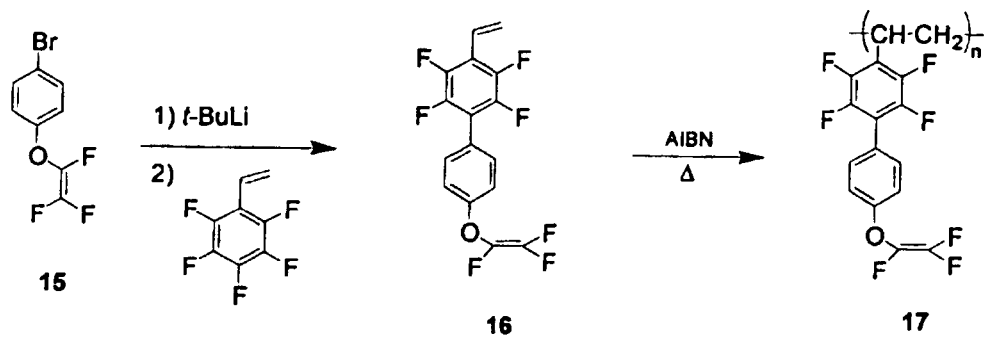
FIG. 7 outlines a synthesis of a crosslinkable polymer used in some embodiments.

Referring to FIG. 7, a three-neck 500 ml flask equipped with a thermometer, a magnetic stirrer bar, and an addition funnel was charged with 25.3 g (0.1 mol) of Compound 15, which can be prepared as in *Macromolecules* 1996, 29(3), 852–860). The flask was purged with nitrogen before introducing 200 mL of dry ether and then was cooled in dry ice-acetone bath. 76 mL of 1.7 M t-BuLi in pentane was dropped into flask from addition funnel below −65° C. After completion of this addition, the reaction was kept in the above bath for 1 hour. 19.4 g of 2,3,4,5,6-pentafluorostyrene was then added and allowed to react for 1 h before removing the cooling bath and letting the temperature reach 0° C. At this moment, dilute HCl aqueous solution was poured into the flask to quench the reaction until the aqueous layer became acidic. The organic layer was separated, dried over $MgSO_4$, evaporated, and purified on a silica gel column with hexanes to give Compound 16 as a white solid (10.08 g, 29%).

A mixture of Compound 16, (1.7411 g, 5.0 mmol), THF (5 mL), and 2,2'-azoisobutyronitrile (AIBN) in a 25 mL flask equipped with a condenser was kept under nitrogen atmosphere at 76° C. for 5 hours and 60° C. overnight. The reaction was allowed to cool and the polymer was collected after precipitation by the addition of hexanes and filtration to give 1.2 g of Polymer 17 as a white powder.

A crosslinked electro-optic polymer thin film including Compound 14 in Polymer 17 was prepared by: 1) preparing a solution of Compound 14 and Polymer 17 (15% by weight loading of Compound 14 with respect to Polymer 17) in cyclopentanone (30% by weight loading of cyclopentanone with respect to Compound 14 and Polymer 17); 2) spin depositing the solution at 500 rpm for 5 sec and 1300 rpm for 30 sec on a 2" ITO substrate; 3) corona poling the system at 180° C. and 4.5 kV for 10 min, 5.5 kV for 5 min, 6.5 kV for 5 min, and 7.5 kV for 5 min; and 4) allowing the crosslinked film to cool to room temperature under the 7.5 kV field.

Other embodiments are within the following claims.

What is claimed is:

1. A nonlinear optical chromophore having the formula D-π-A, wherein π is a π bridge including a thiophene ring having oxygen atoms bonded directly to the 3 and 4 positions of the thiophene ring, D is a donor, and A is an acceptor.

2. The chromophore of claim 1, wherein the oxygen atoms are independently substituted with an alkyl, heteroalkyl, aryl, or heteroaryl group.

3. A nonlinear optical chromophore having the formula:

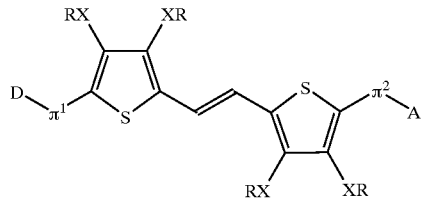

wherein, independently at each occurrence: $\pi^1$ is absent or a π-bridge; $\pi^2$ is absent or a π-bridge; D is an donor; A is an acceptor; X is O or S; and R is an alkyl, aryl, heteroalkyl, or heteroaryl group.

4. The chromophore of claim 1, 2, or 3 wherein the donor is selected from the group consisting of:

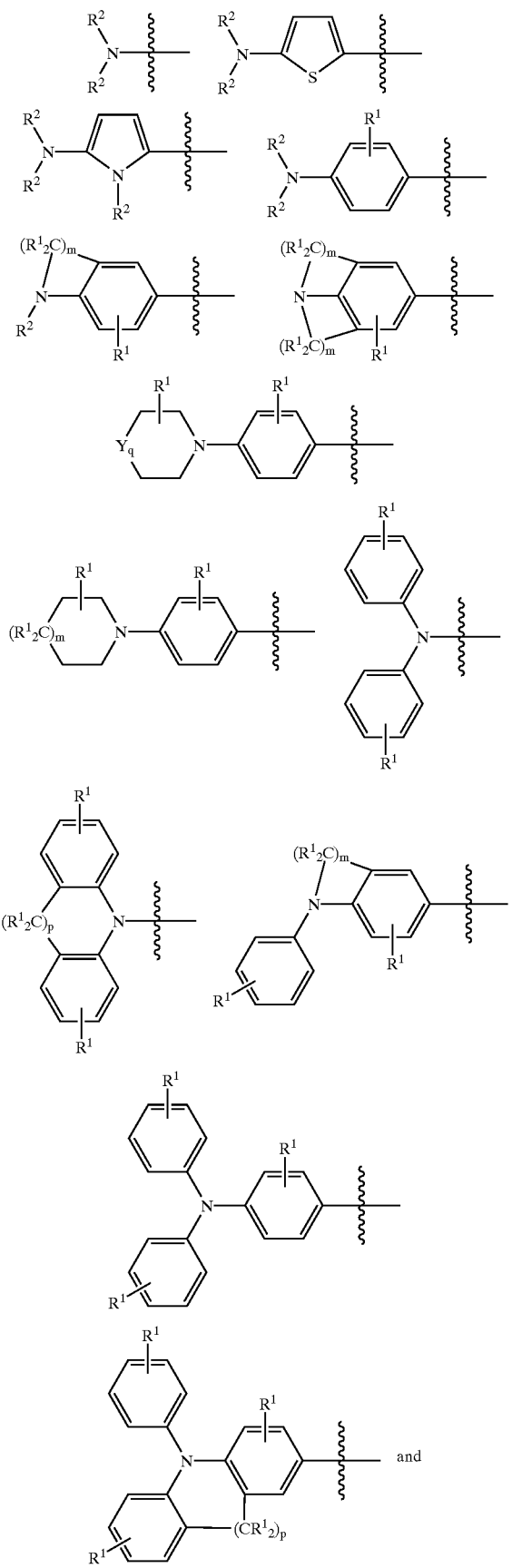

-continued

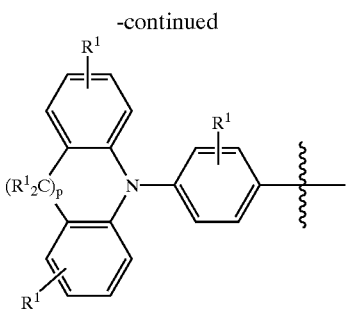

and the acceptor is selected from the group consisting of

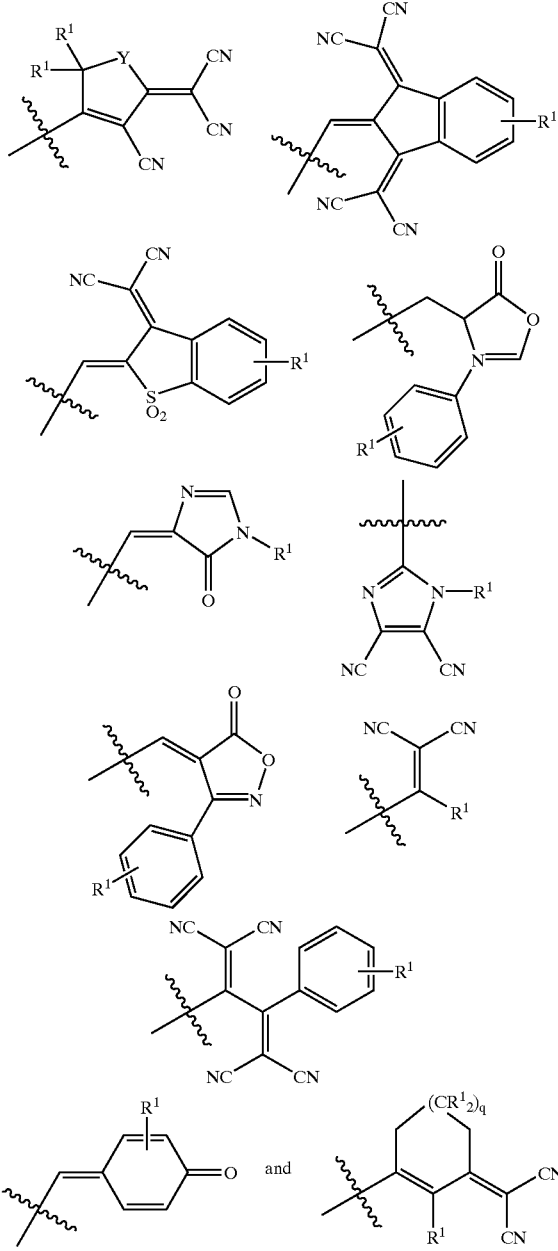

wherein independently at each occurrence: $R^1$ is hydrogen, a halogen except when bonded to a carbon alpha to or directly to a nitrogen, oxygen, or sulfur atom, or an alkyl, aryl, heteroalkyl, or heteroaryl group; $R^2$ is hydrogen or an alkyl, aryl, heteroalkyl, or heteroaryl group; Y is O, S or Se; m is 2, 3 or 4; p is 0, 1 or 2; and q is 0 or 1.

5. The chromophore of claim 4, wherein the donor is selected from the group consisting of

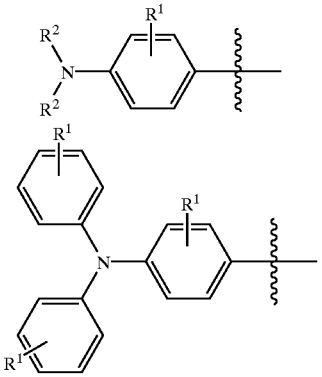

wherein, independently at each occurrence: $R^1$ is hydrogen, a halogen except when bonded to a carbon alpha to or directly to a nitrogen, oxygen, or sulfur atom, or an alkyl, aryl, heteroalkyl, or heteroaryl group; and $R^2$ is hydrogen or an alkyl, aryl, heteroalkyl, or heteroaryl group.

6. The chromophore of claim 3, wherein each X is oxygen and each R group is an alkyl group.

7. A second order nonlinear optical composition comprising a polymer matrix and a chromophore according to claim 1, 2, or 3.

8. The composition of claim 7, wherein the chromophore is covalently incorporated into the polymer matrix.

9. The composition of claim 7, wherein the polymer matrix is crosslinked.

10. The composition of claim 8, wherein the polymer matrix is crosslinked.

11. An electro-optic device, comprising the second order nonlinear optical composition of claim 7.

12. The electro-optic device of claim 11, wherein the electro-optic device is selected from the group consisting of an optical modulator, an optical switch, and an optical directional coupler.

13. The electro-optic device of claim 11, comprising: 1) an input waveguide; 2) an output waveguide; 3) a first leg having a first end and a second end, the first leg being coupled to the input waveguide at the first end and to the output waveguide at the second end; and 4) and a second leg having a first end and a second end, the second leg being coupled to the input waveguide at the first end and to the output waveguide at the second end.

14. The electro-optic device of claim 11, comprising: 1) an input; 2) an output; 3) a first waveguide extending between the input and output; and 4) a second waveguide aligned to the first waveguide and positioned for evanescent coupling to the first waveguide.

15. An optical router including the electro-optic device of claim 11.

16. A communications system including at least one electro-optic device of claim 11.

17. A method of data transmission comprising transmitting light through the composition of claim 7.

18. A method of telecommunication comprising transmitting light through the composition of claim 7.

19. A method of transmitting light comprising directing light through or via the composition of claim 7.

20. A method of routing light through an optical system comprising transmitting light through or via the composition of claim 7.

21. A phased array radar system comprising the composition of claim 7.

* * * * *

UNITED STATES PATENT AND TRADEMARK OFFICE
CERTIFICATE OF CORRECTION

PATENT NO.     : 6,750,603 B2
DATED          : June 15, 2004
INVENTOR(S)    : Diyun Huang and Baoquan Chen It is certified that error appears in the above-identified patent and that said Letters Patent is hereby corrected as shown below:

Title page,
Item [75], Inventors, please delete "US" and insert -- China -- therefor; (both occurrences);
Item [56], References Cited, OTHER PUBLICATIONS,
"Smith and Babb" reference, please delete "SiloxaneContaining" and insert -- Siloxane-Containing -- therefor;

Column 4,
Line 45, please delete the second structure and insert -- 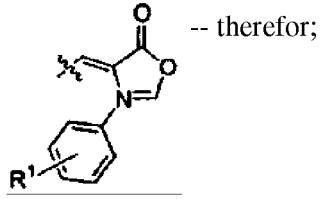 -- therefor;

Column 9,
Line 63, please delete "an" first occurrence, and insert -- a -- therefor;

Column 11,
Line 27, please delete the second structure and insert -- 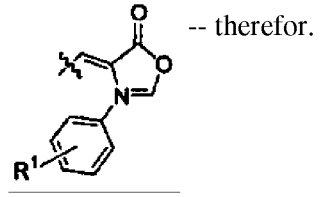 -- therefor.

Signed and Sealed this

Twenty-fourth Day of May, 2005

JON W. DUDAS
*Director of the United States Patent and Trademark Office*